United States Patent [19]

Gaster et al.

[11] Patent Number: 5,696,122
[45] Date of Patent: Dec. 9, 1997

[54] INDOLE AND INDOLINE DERIVATIVES AS 5HT$_{1D}$ RECEPTOR ANTAGONISTS

[75] Inventors: Laramie Mary Gaster; David Malcolm Duckworth, both of Bishop's Stortford; Sarah Margaret Jenkins, Harlow; Paul Adrian Wyman, Epping, all of England

[73] Assignee: SmithKline Beecham p.l.c., England

[21] Appl. No.: 605,022

[22] PCT Filed: Aug. 9, 1994

[86] PCT No.: PCT/EP94/02663

§ 371 Date: Feb. 26, 1996

§ 102(e) Date: Feb. 26, 1996

[87] PCT Pub. No.: WO95/06637

PCT Pub. Date: Mar. 9, 1995

[30] Foreign Application Priority Data

| | | | |
|---|---|---|---|
| Sep. 3, 1993 | [GB] | United Kingdom | 9318325 |
| Sep. 3, 1993 | [GB] | United Kingdom | 9318337 |
| Oct. 28, 1993 | [GB] | United Kingdom | 9322251 |
| Oct. 28, 1993 | [GB] | United Kingdom | 9322252 |
| Dec. 16, 1993 | [GB] | United Kingdom | 9325753 |

[51] Int. Cl.$^6$ ............... A61K 31/495; C07D 403/10; C07D 403/14; C07D 413/14
[52] U.S. Cl. ............... 514/254; 544/364; 544/367; 544/373
[58] Field of Search ............... 514/254, 255; 544/367, 364, 373

[56] References Cited

U.S. PATENT DOCUMENTS

| | | | |
|---|---|---|---|
| 4,895,849 | 1/1990 | Yoshioka et al. | 514/241 |
| 5,202,329 | 4/1993 | Ishikawa et al. | 514/274 |
| 5,340,810 | 8/1994 | Clithrow et al. | 514/252 |
| 5,356,893 | 10/1994 | Bradshaw et al. | 514/227.2 |
| 5,358,948 | 10/1994 | Bradshaw et al. | 514/252 |
| 5,387,748 | 2/1995 | Demuth et al. | 514/254 |
| 5,424,313 | 6/1995 | Hartog et al. | 514/254 |

FOREIGN PATENT DOCUMENTS

| | | | |
|---|---|---|---|
| 0 533 266 A1 | 3/1993 | European Pat. Off. | C07D 295/135 |
| 0 533 267 A1 | 3/1993 | European Pat. Off. | C07D 213/56 |
| 0 533 268 A1 | 3/1993 | European Pat. Off. | C07D 271/06 |
| WO 84/02133 | 6/1984 | WIPO | C07D 209/08 |

OTHER PUBLICATIONS

Chemical Abstracts, vol. 68, No. 15, 8 Apr. 1968, abstract No. 68881x, p. 6645.

*Primary Examiner*—Mukund J. Shah
*Assistant Examiner*—Sabiha N. Qazi
*Attorney, Agent, or Firm*—Wayne J. Dustman; Charles M. Kinzig; Edward T. Lentz

[57] ABSTRACT

The present invention provides novel indole and indoline derivatives according to formula (I) below, processes for their preparation, pharmaceutical compositions containing them and their use as medicaments. The present indole and indoline derivatives are compounds of formula (I) or a salt thereof:

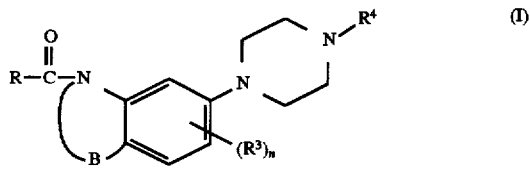

in which
R is a group of formula (i):

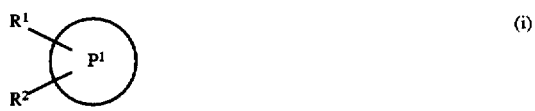

in which $P^1$ is a phenyl or a 5 to 7-membered heterocyclic ring containing 1 to 3 heteroatoms selected from oxygen, nitrogen or sulphur; and $R^1$ and $R^2$ are independently hydrogen, halogen, $C_{1-6}$alkyl, $C_{1-6}$alkoxy, hydroxy$C_{1-6}$alkyl, acyl, nitro, trifluoromethyl, cyano, $SR^5$, $SOR^5$, $SO_2R^5$, $SO_2NR^5R^6$, $CO_2R^5$, $CONR^5R^6$, $CONR^5(CH_2)_xCO_2R^6$, $NR^5R^6$, $NR^5CO_2R^6$, $CR^5=NOR^6$, where $R^5$ and $R^6$ are independently hydrogen or $C_{1-6}$alkyl and x is 1 to 3;

or R is a group of formula (ii):

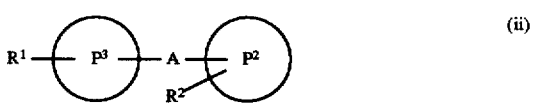

in which $P^2$ is phenyl or biphenyl;

$P_3$ is phenyl or a 5 to 7-membered heterocyclic ring containing 1 to 3 heteroatoms selected from oxygen, nitrogen or sulphur;

A is a bond or a group $(CH_2)_p$—$R^8$—$(CH_2)_q$ where $R^8$ is oxygen, $S(O)_m$ where m is 0 to 2, carbonyl, $CO_2$ or $CH_2$ and p and q are independently 0 to 3; and $R^1$ and $R^2$ are as defined above in formula (i);

$R^3$ is hydrogen, halogen, hydroxy, $C_{1-6}$alkyl or $C_{1-6}$alkoxy;

n is 1 or 2;

$R^4$ is hydrogen or $C_{1-6}$alkyl; and

B is —$CHR^9CHR^{10}$— or —$CR^9$=$CR^{10}$— where $R^9$ and $R^{10}$ are independently hydrogen or $C_{1-6}$alkyl.

$C_{1-6}$alkyl groups, whether alone or as part of another group, may be straight chain or branched.

The groups $P_1$, $P_2$, and $P_3$ can be aromatic or saturated heterocyclic rings.

9 Claims, No Drawings

INDOLE AND INDOLINE DERIVATIVES AS 5HT$_{1D}$ RECEPTOR ANTAGONISTS

The present application is filed under § 371 and is based on PCT application number PCT/EP94/02663, filed on Aug. 9, 1993, which, in turn, is based on Great Britain application number 9318325.9, filed on Sep. 3, 1993, Great Britain application number 9318337.4, filed on Sep. 3, 1993, Great Britain application number 9322251.1, filed on Oct. 28, 1993, Great Britain application number 9322252.9, filed on Oct. 28, 1993 and Great Britain application number 9325753.3, filed on Dec. 16, 1993.

The present invention relates to novel urea derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are alleged to be of use in the treatment of various CNS disorders such as depression.

A structurally distinct class of compounds have now been discovered and have been found to exhibit 5HT$_{1D}$ antagonist activity. In a first aspect, the present invention therefore provides a compound of formula (I) or a salt thereof:

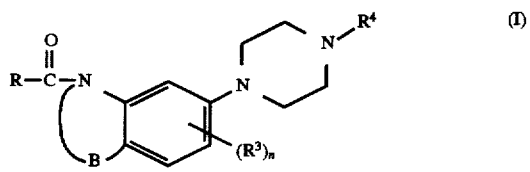

in which
R is a group of formula (i):

in which P$^1$ is a phenyl or a 5 to 7-membered heterocyclic ring containing 1 to 3 heteroatoms selected from oxygen, nitrogen or sulphur;, and R$^1$ and R$^2$ are independently hydrogen, halogen, C$_{1-6}$alkyl, C$_{1-6}$alkoxy, hydroxyC$_{1-6}$alkyl, acyl, nitro, trifluoromethyl, cyano, SR$^5$, SOR$^5$, SO$_2$R$^5$, SO$_2$NR$^5$R$^6$, CO$_2$R$^5$, CONR$^5$R$^6$, CONR$^5$(CH$_2$)$_x$CO$_2$R$^6$, NR$^5$R$^6$, NR$^5$CO$_2$R$^6$, CR$^5$=NO R$^5$ and R$^6$ are independently hydrogen or C$_{1-6}$alkyl and x is 1 to 3;

or R is a group of formula (ii):

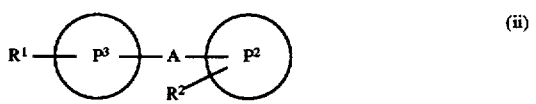

in which P$^2$ is phenyl or biphenyl;

P$^3$ is phenyl or a 5 to 7-membered heterocyclic ring containing 1 to 3 heteroatoms selected from oxygen, nitrogen or sulphur;, A is a bond or a group (CH$_2$)$_p$—R$^8$—(CH$_2$)$_q$ where R$^8$ is oxygen, S(O)$_m$ where m is 0 to 2, carbonyl, CO$_2$ or CH$_2$ and p and q are independently 0 to 3; and R$^1$ and R$^2$ are as defined above in formula (i);

R$^3$ is hydrogen, halogen, hydroxy, C$_{1-6}$alkyl or C$_{1-6}$alkoxy;

n is 1 or 2;

R$^4$ is hydrogen or C$_{1-6}$alkyl; and

B is —CHR$^9$CHR$^{10}$— or —CR$^9$=CR$^{10}$— where R$^9$ and R$^{10}$ are independently hydrogen or C$_{1-6}$alkyl.

C$_{1-6}$alkyl groups, whether alone or as part of another group, may be straight chain or branched.

The groups P$^1$, P$^2$, and P$^3$ can be aromatic or saturated heterocyclic rings. Examples of aromatic heterocyclic rings include thienyl, furyl, pyrrolyl, triazolyl, diazolyl, isothiazolyl, oxadiazolyl, isoxazolyl, thiadiazolyl, pyridyl, pyrimidyl and pyrazinyl. Examples of saturated rings include piperidine, morpholine and piperazine rings. Each of the groups P$^1$, P$^2$, and P$^3$ can be linked to the remainder of the molecule via a carbon atom or, when present, a nitrogen atom.

When R is a group of formula (i) P$^1$ is preferably phenyl, R$^1$ is preferably halogen and R$^2$ is preferably C$_{1-6}$alkyl, for example methyl.

Preferred groups of formula (ii) include those in which P$^2$ and P$^3$ are both phenyl and A is oxygen and those in which P$^2$ is biphenyl, A is a bond and P$^3$ is a 5 to 7-membered heterocyclic ring containing 1 to 3 heteroatoms selected from oxygen, nitrogen or sulphur. More preferably P$^3$ is a 5-membered ring containing 3 heteroatoms, in particular a 1,2,4-oxadiazol-3-yl group. When R is a group of formula (ii) R$^1$ and R$^2$ are preferably C$_{1-6}$alkyl in particular methyl. When P$^2$ is a biphenyl group one or more R$^2$ substituents can be present.

Most preferably R is a group of formula (ii) having the following structure:

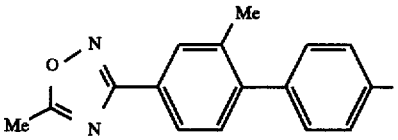

Suitably R$^3$ is hydrogen, halogen, hydroxy, C$_{1-6}$alkyl or C$_{1-6}$alkoxy. Preferably R$^3$ is C$_{1-6}$alkoxy such as methoxy.

Preferably n is 1.

Suitably R$^4$ is hydrogen or C$_{1-6}$alkyl. Preferably R$^4$ is hydrogen or C$_{1-4}$alkyl such as methyl.

Preferably R$^9$ and R$^{10}$ are both hydrogen such that the group B forms part of an indole or indoline ring.

Particularly preferred compounds include:
1-[3-methyl-4-(4-pyridyl)benzoyl]-2,3-dihydro-5-methoxy-6-(4-methyl-1-piperazinyl)]1H-indole,
1-(4-bromo-3-methylbenzoyl)-2,3-dihydro-5-methoxy-6-(4-methyl-1-piperazinyl)-1-H-indole,
1-(4-bromo-3-methylbenzoyl)-5-methoxy-6-(4-methyl-1-piperazinyl)-1H-indole,
2,3-dihydro-5-methoxy-6-(4-methyl-1-piperazinyl)-1-[2'-bromo-3'-methoxythiophene-4'-ylcarbonyl]indole,
2,3-dihydro-5-methoxy-6-(4-methyl-1-piperazinyl)-1-[4'-phenoxybenzoyl]indole,
2,3-dihydro-5-methoxy-1-[4-(2-methyl-4-(5-methyl-1,2,4-oxadiazol-3-yl)phenyl) benzoyl]-6-(4-methyl-1-piperazinyl)-1H-indole,
5-methoxy-1-[4-(2-methyl-4-(5-methyl-1,2,4-oxadiazol-3-yl)phenyl)benzoyl]-6-(4-methyl-1-piperazinyl)-1H-indole, or
2,3-dihydro-5-methoxy-1-[4-(2-methyl-4-(5-methyl-1,2,4-oxadiazol-3-yl)phenyl) benzoyl]-6-(1-piperazinyl)-1H-indole, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates.

In a further aspect the present invention provides a process for the preparation of a compound of formula (I) which comprises:

(a) coupling a compound of formula (II):

R—COL                (II)

in which R is as defined in formula (I) and L is a leaving group with a compound of formula (III):

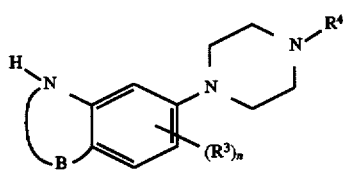

(III)

in which $R^3$, $R^4$, B and n are as defined in formula (I);

(b) for compounds where R is a group of formula (ii), A is a bond and $P^2$ is a phenyl group, reaction of a compound of formula (IV):

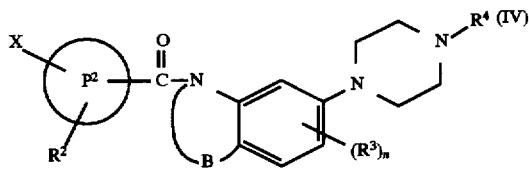

(IV)

in which $R^2$, $R^3$, $R^4$ and n are as defined in formula (I), $P^2$ is phenyl and X is a leaving group with a nucleophile $R^1$—$P^3$ where $R^1$ and $P^3$ are as defined in formula (I);

(c) reaction of a compound of formula (V):

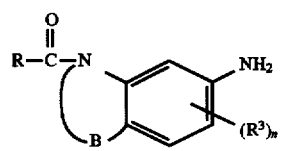

(V)

in which R, $R^3$, B and n are as defined in formula (I) with a compound of formula (VI):

$R^4N(CH_2CH_2Hal)_2$        (VI)

in which $R^4$ is as defined in formula (I) and Hal is halogen, or (d) for compounds where R is a group of formula (ii) and A is a bond, reaction of a compound of formula (VII):

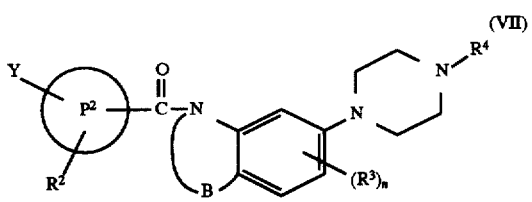

(VII)

in which $P^2$, $R^2$, $R^3$, $R^4$, B and n are as defined in formula (I) and Y is halogen or a group —$OSO_2CF_3$ with a compound of formula (VIII):

(VIII)

in which $R^1$ and $P^3$ are as defined in formula (I), or (e) for compounds where R is a group of formula (ii) and A is a bond, reaction of a compound of formula (IX):

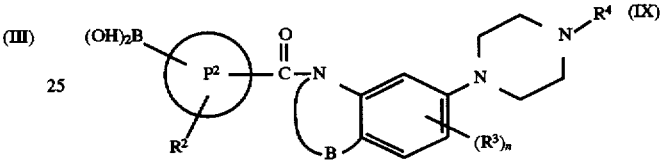

(IX)

in which $P^2$, $R^2$, $R^3$, $R^4$, B and n are as defined in formula (I) with a compound of formula (X):

(X)

in which $R^1$ and $P^3$ are as defined in formula (I) and Y is as defined in formula (VII), and optionally after any of the above processes:

converting a compound of formula (I) into another compound of formula (I)

forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazole. Preferably the group L is halo, particularly chloro.

A compound of formula (II) is typically reacted with a compound of formula (III) in an inert organic solvent such as DMF, THF or dichloromethane at ambient or elevated temperature in the presence of a base such as triethylamine or pyridine. In the case of indoles a base such as KO$^t$Bu is required.

Compounds of formula (II) can be prepared from a compound of formula (XI):

$RCO_2H$               (XI)

in which R is as defined in formula (I) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Reaction of a compound of formula (IV) with a nucleophile $R^1$—$P^3$ is preferably carried out in a suitable solvent such as dimethylformamide in the presence of a strong base such as sodium hydride. Preferably the leaving group X is halo, in particular fluoro. Preferably the group $R^2$ is an electron withdrawing group, for example nitro, $COCH_3$ or cyano, in the ortho or para-positions relative to the group X.

Reaction of a compound of formula (V) with a compound of formula (VI) is suitably carried out in an alcohol or nitrile solvent with an optional base or, alternatively, in a non-polar solvent such as chlorobenzene in the absence of base. Suitably, the reactions are carried out at ambient or elevated temperature, preferably at the reflux temperature of the reaction mixture.

Reaction of compounds of formula (VII) and (VIII) and reaction of compounds of formulae (IX) and (X) can be carried out in the presence of a transition metal catalyst such as $Pd(PPh_3)_4$ in a solvent such as an ether in the presence of a base such as an alkali metal carbonate or bicarbonate, for example sodium carbonate or bicarbonate, at ambient or elevated temperature.

Intermediate compounds of formulae III, (III), (IV), (V), (VI), (VII), (VIII), (IX), (X) and (XI) are commercially available or can be prepared using standard procedures such as those outlined in EPA 533266/7/8.

It will be appreciated by those skilled in the art that it may be necessary to protect certain reactive substituents during some of the above procedures, for example when the group $R^4$ is a hydrogen atom. Suitable protecting groups and methods for their attachment and removal are conventional in the an of organic chemistry, such as those described in Greene T. W. 'Protective groups in organic synthesis' New York, Wiley (1981).

For example, secondary amines can be protected as benzyl, benzyloxycarbonyl or trityl derivatives. These groups can be removed by conventional procedures.

Carboxylic acid groups can be protected as esters. Aldehyde or ketone groups can be protected as acetals, ketals, thioacetals or thioketals. Deprotection is achieved using standard conditions.

Compounds of formula (I) can be convened into further compounds of formula (I) using standard techniques. For example, in the case wherein $R^4$ is hydrogen, it is possible to introduce a $C_{1-6}$alkyl group by conventional alkylation using 1 molar equivalent of a $C_{1-6}$alkyl halide and 1 molar equivalent of a suitable base in an inert solvent. Compounds of formula (I) in which $R^1$ or $R^2$ are acid groups can be esterified using normal procedures.

$5HT_{1D}$ Antagonists, and in particular the compounds of the present invention, may therefore be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective mount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

When administered in accordance with the invention, no unacceptable toxicological effects are expected with the compounds of the invention.

The following Examples illustrate the preparation of compounds of the invention.

Intermediate 1

N-[4-methoxy-3-(4-methyl-1-piperazinyl)phenyl] aminoacetaldehyde dimethyl acetal A suspension of 4-methoxy-3-(4-methyl-1-piperazinyl) benzenamine (5 g, 0.023 mol) in ethanol (150 ml) and dimethoxyethanal (9.5 g, 1.2 eq) was hydrogenated over 10% Palladium on charcoal (3 g) at standard temperature and pressure for 3 h. The suspension was filtered through kieselguhr, washed with methanol and evaporated to give a pale yellow oil. Purification by Fcc, eluting with 2% methanol/dichloromethane afforded the title compound (6.64 g, 95%).

$^1$H NMR (250 MHz, CDCl$_3$) δ: 2.38 (3H, s), 2.63 (4H, br s), 3.11 (4H, br s), 3.21 (2H, d, J=6), 3.42 (6H, s), 3.81 (3H, s), 4.58 (1H, t, J=2), 6.27 (1H, m), 6.32 (1H, m), 6.72 (1H, d, J=6).

Intermediate 2

1-H-[5-methoxy-6-(4-methyl-1-piperazinyl)]indole

A solution of intermediate 1, (6.6 g, 0.02 mol) in TFA (27 ml) at 0° C. was treated with TFAA (27 ml) under an argon atmosphere. More TFA (40 ml) was added and the reaction was heated to reflux for 48 h. The solution was evaporated to dryness and the residue taken up in ethyl acetate, washed with saturated sodium bicarbonate solution, and water (3x), dried (Na$_2$SO$_4$) and evaporated to give the title compound as a brown solid (1.21 g, 71%).

$^1$H NMR (250 MHz, CDCl$_3$) δ: 2.70 (3H, s), 2.67 (4H, br s), 3.12 (4H, br s), 3.90 (3H, s), 6.45 (1H, m), 7.0 (1H, s), 7.08 (1H, s), 7.12 (1H, m), 8.21 (1H, br s).

Intermediate 3

2,3-Dihydro-5-methoxy-6-(1-piperazinyl)-1H-indole

Intermediate 2 (0.5 g, 2 mmol) in glacial acetic acid was treated with sodium cyanoborohydride (0.75 g, 1.2 mmol) at room temperature with stirring for 1 h. The mixture was diluted with water and basified with 10% aq. NaOH. The product was extracted into dichloromethane (3x), dried (Na$_2$SO$_4$), filtered and evaporated to give the title compound as a brown solid (0.49 g, 99%).

$^1$H NMR (250 MHz, CDCl$_3$) δ: 2.72 (3H, s), 3.0 (2H, t, J=6), 3.15 (4H, br s), 3.23 (4H, br s), 3.55 (2H, t, J=6), 3.80 (3H, s), 6.39 (1H, s), 6.77 (1H, s)

Intermediate 4

2,3-Dihydro-5-methoxy-6-(1-piperazinyl)-1H-indole

A stirred solution of intermediate 3 (280 mg, 1.1 mmole) in 1,2-dichloroethane (15 ml) at room temperature under argon was treated with 1-chloroethyl chloroformate (0.31 ml, 2.8 mmole). The mixture was kept at room temperature for 1 h, then treated with diisopropylethylamine (0.25 ml, 1.5 mmole) and heated under reflux for 2 h. The reaction mixture was concentrated in vacuo, the residue treated with methanol (10 ml) and heated under reflux for 1 h. The solution was concentrated under vacuum and the residue basified with 10% Na$_2$CO$_3$ solution (20 ml) and extracted with dichloromethane (2x20 ml). The combined extract was dried (Na$_2$SO$_4$) and concentrated under vacuum to afford the title compound as a brown oil (270 mg, 100%).

$^1$H NMR (250 MHz) CDCl$_3$ δ: 6.72 (1H, s), 6.38 (1H, s), 3.79 (3H, s), 3.52 (2H, t), 2.6–3.1 (12 m).

Intermediate 5

2,3-Dihydro-5-methoxy-6-(4-tert-butoxycarbonyl-1-piperazinyl)-1H-indole

A stirred solution of intermediate 4 (270 mg, 1.1 mmole) and triethylamine (0.30 ml, 2.2 mmole) in dichloromethane (8 ml) was treated with a solution of di-tert-butyl dicarbonate (200 mg, 1.0 mmole) in dichloromethane (5 ml) and the mixture kept at room temperature for 3 h, then treated with 10% Na$_2$CO$_3$ solution (10 ml) and extracted with dichloromethane (2x15 ml). The combined extract was dried (Na$_2$SO$_4$), concentrated under vacuum, and the residue chromatographed on silica gel eluting with ethyl acetate to afford the title compound as a beige solid (130 mg, 38%).

$^1$H NMR (250 MHz) CHCl$_3$ δ: 6.74 (1H, s), 6.34 (1H, s), 3.80 (3H, s), 3.48–3.64 (7H, m), 2.90–3.05 (6H, m), 1.48 (9H, s)

EXAMPLE 1

1-(4-bromo-3-methylbenzoyl)-2,3-dihydro-5-methoxy-6-(4-methyl-1-piperazinyl)-1H-indole A solution of intermediate 3 (220 mg, 0.89 mmol), in dry THF (24 ml) and water (24 ml) containing sodium hydroxide (0.546 g) was treated with a solution of 4-bromo 3-methyl benzoyl chloride (870 mg, 1.58 mmol) in dry THF (10 ml). The resulting mixture was stirred at room temperature for 4 h then water was added and the mixture was extracted with dichloromethane (3x). The organic layers were combined, dried (Na$_2$ SO$_4$), filtered and concentrated in vacuo to give the title compound as a yellow foam. Purification by FCC eluting with 1% methanol/ dichloromethane gave the product as a pale yellow oil (0.5 g, 12%).

$^1$H NMR (250 MHz, CDCl$_3$) δ: 2.38 (3H, s), 2.42 (3H, s), 2.67 (5H, br s), 3.02–3.17 (5H, m), 3.87 (3H, s), 3.89 (1H,br s), 4.21 (1H, br s), 6.72 (1H, s), 7.21 (1H, d, J=6), 7.41 (1H, s), 7.61 (1H, d, J=6), 7.98 (1H, br s).

EXAMPLE 2

1-[3-methyl-4-(-4-pyridyl)phenyl]-2,3-dihydro-5-methoxy-6-(4-methyl-1-piperazinyl)]-1H-indole A mixture of example 1 (0.13 g, 0.29 mmol), 4-pyridinylboronic acid (0.04 g, 0.29 mmol), tetrakis (triphenylphosphine) palladium (0) (15 mg) and aqueous sodium carbonate (2N; 1.5 ml) and DME (5 ml) was heated at reflux under argon for 48 h. The reaction mixture was then cooled to room temperature, added to water and extracted with dichloromethane (3×). The combined organic layers were dried ($Na_2SO_4$) and concentrated in vacuo to give an oil. Purification by FCC, eluting with 2% methanol/ dichloromethane afforded the title compound (0.07 g, 35%).

$^1$H NMR (250 NHz, $CDCl_3$) δ: 2.32 (3H, s), 2.38 (3H, s), 2.68 (5H, br s), 3.07–3.18 (5H, br s), 3.85 (3H, s), 4.10 (1H, br s), 4.28 (1H, br s), 6.78 (1H, s), 7.30 (3H, m), 7.45–7.5 (2H, m), 8.02 (1H, br s), 8.7 (2H, d, J=6).

EXAMPLE 3

1-(4-bromo-3-methylbenzoyl)-5-methoxy-6-(4-methyl-1-piperazinyl)-1H-indole

To a mixture of intermediate 2 (0.25 g, 1.0 mmol) and potassium t-butoxide (0.114 g, 1 mmol) in dry THF (15 ml) was added 4-bromo-3-methyl benzoyl chloride (0.238 g, 1.0 mmol) in dry THF (10 ml). The resulting mixture was stirred at room temperature for 72 h, then poured onto water and extracted with dichloromethane (3×). The organic layers were combined, dried ($Na_2SO_4$), filtered and concentrated in vacuo to give the crude product Purification by Fcc eluting with 3% methanol/dichloromethane gave the title compound as a pale yellow oil (70 mg, 15%).

$^1$H NMR (250 MHz, $CDCl_3$) δ: 2.41 (3H, s), 2.49 (3H, s), 3.12 (4H, br s), 3.44 (4H, br s), 3.92 (3H, s), 6.5 (1H, d, J=2), 7.03 (1H, s), 7.12 (1H, d, J=2), 7.39 (1H, d, J=6), 7.53 (1H, m), 7.58 (1H, d, J=6).

EXAMPLE 4

2,3-Dihydro-5-methoxy-6-(4-methyl-1-piperazinyl)-1-[2'-bromo-3'-methoxythiophene-4'-ylcarbonyl]indole A solution of intermediate 4 (0.2 g) in a mixture of THF (5 ml) and aqueous sodium hydroxide (0.1 g in 5 ml of $H_2O$) was treated with a solution of 4-bromo-3-methoxythiophene-2-carboxylic acid chloride (0.3 1 g) in THF (5 ml). The reaction mixture was stirred at room temperature for 10 hours, poured into water, and extracted with dichloromethane. The combined organic extracts were dried over sodium sulphate and concentrated in vacuo to give the title compound as a brown oil (0.21 g, 53%).

$^1$H NMR (250MHz, $CDCl_3$) δ: 2.40 (3H s), 2.67 (4H, br s), 3.04–3.17 (6H, m), 3.82–4.02 (8H, m), 6.78 (1H, s) 7.41 (1H, s), 8.01 (1H, s)

EXAMPLE 5

2,3-Dihydro-5-methoxy-6-(4-methyl-1-piperazinyl)-1-[4'-phenoxybenzoyl]indole

A solution of intermediate 4, (0.2 g) in THF (2 ml) and sodium hydroxide (0.1 g in 2 ml $H_2O$) was treated with a solution of 4-phenoxybenzoyl chloride (0.28 g) in THF (5 ml). The reaction was stirred overnight, poured into water and extracted with dichloromethane. The combined extracts were dried over sodium sulphate and concentrated to give an oil which was purified by column chromatography using $CH_2Cl_2$ to 96% $CH_2Cl_2$/4% MeOH as eluent. The title compound was obtained as a pale yellow oil.

$^1$H NMR (250 MHz, $CDCl_3$) δ: 2.41 (3H, s), 2.69 (4H, br s), 2.97–3.14 (6H, m), 3.84 (3H, s), 4.11 (2H, br s), 6.77 (1H, s), 6.95–7.08 (5H, m), 7.19 (1H, t, J=6), 7.39 (2H, t, J=6), 7.53 (2H, d, J=6).

EXAMPLE 6

2,3-Dihydro-5-methoxy-1-[4-(2-methyl-4-(5-methyl-1,2,4-oxadiazol-3-yl)phenyl) benzoyl]-6-(4-methyl-1-piperazinyl)-1H-indole 2'-Methyl-4'-(5-methyl-1,2,4-oxadiazol-3-yl)[1,1'-biphenyl]-4-carboxylic acid (EP 0 533 268 A1-Intermediate 42) (410 mg, 0.0014 mole) was treated with thionyl chloride (15 ml) and heated under reflux for 2h. The solution was concentrated in vacuo in leave the acid chloride as a yellow oil. This was dissolved in dry THF (5 ml) and added at room temperature to a stirred solution of intermediate 3 (300 mg, 0.0012 mole) in THF (20 ml) and $H_2O$ (10 ml) containing sodium hydroxide (100 mg, 0.0024 mole). The mixture was stirred at room temperature for 20 h, then concentrated in vacuo to approx. 15 ml volume and extracted with dichloromethane (2×40 ml). The combined extracts were dried ($Na_2SO_4$) and concentrated in vacuo to leave a yellow oil, which was crystallised from ethyl acetate/60–80 petrol to afford the title compound as a beige solid (500 mg, 80%), mp 213°–214° C.

$^1$H NMR (270 MHz, 80° C., $CDCl_3$) δ: 7.97 (1H, s), 7.93 (1H, d), 7.60 (2H, d), 7.40 (2H, d), 7.31 (1H, d), 6.73 (1H, s), 4.13 (2H, t), 3.82 (3H, s), 3.05 (2H, t), 2.97 (4H, br s), 2.63 (3H, s), 2.47–2.55 (4H, m), 2.34 (3H, s), 2.29 (3H, s), 1 aromatic proton too broad to observe.

EXAMPLE 7

5-Methoxy-1-[4-(2-methyl-4-(5-methyl-1,2,4-oxadiazol-3-yl)phenyl)benzoyl]-6-(4-methyl-1-piperazinyl)-1H-indole A stirred solution of intermediate 2 (300 mg, 0.0012 mole) in dry THF (30 ml) under argon was treated with potassium t-butoxide (140 mg, 0.0012 mole) and kept at room temperature for 20 minutes. The resulting mixture was treated with a solution of 4-[2-methyl-4-(5-methyl-1,2,4-oxadiazol-3-yl)phenyl]benzoyl chloride (0.0014 mole) in dry THF (10 ml) and the mixture stirred at room temperature for 20h. The solution was concentrated in vacuo and the residue treated with 10% $Na_2CO_3$ solution (20 ml) and extracted with dichloromethane (2×40 ml). The combined extract was dried ($Na_2SO_4$), concentrated in vacuo and the residue chromatographed on silica gel eluting with 0–3% methanol/dichloromethane. The tide compound was obtained as a yellow solid on crystallisation from ethyl acetate/60–80 petrol (220 mg, 35%) mp 175°–177° C.

$^1$H NMR (250 MHz, $CDCl_3$) δ: 2.39 (6H, s), 2.68 (7H, br s), 3.20 (4H, br s), 3.95 (3H, s), 6.55 (1H, d), 7.05 (1H, s), 7.28 (1H, d), 7.38 (1H, d), 7.51 (2H, d), 7.82 (2H, d), 7.99 (1H, d), 8.04 (1H, s), 8.10 (1H, s)

EXAMPLE 8

2,3-Dihydro-5-methoxy-1-[4-(2-methyl-4-(5-methyl-1,2,4-oxadiazol-3-yl)phenyl) benzoyl]-6-(1-piperazinyl)-1H-indole 2'-Methyl-4'-(5-methyl-1,2,4-oxadiazol-3-yl)[1,1'-biphenyl]-4-carboxylic acid (EP 0 533 268 A1 Intermediate 42) (205 mg, 0.70 mmole) was treated with thionyl chloride (5 ml) and heated under reflux for 2h. The solution was concentrated under vacuum to leave the acid chloride as a yellow oil. This was dissolved in dry THF (5 ml) and added to a stirred solution of intermediate 5 (205 mg, 0.61 mmole) in THF (5 ml) and $H_2O$ (5 ml) containing NaOH (56 mg, 1.4 mmole). The mixture was stirred at room temperature for 0.5 h, then diluted with H$_2$O (20 ml) and extracted with ethyl acetate (2×25 ml). The combined extract was dried (Na$_2$SO$_4$) and concentrated under vacuum. The residual material crystallised from ethyl acetate/ether to afford a white solid (280 mg). This was dissolved in methanol (10 ml), treated with ether/HCl (2 ml of 3.3M solution) and left at room temperature for 20 h. The solid which had crystallised out was filtered off and dried to afford the hydrochloride salt of the title compound as a beige solid (190 mg) mp 153°–155° C.

HCl salt: $^1$H NMR (250 MHz) d$^6$DMSO δ: 9.45 (2H, br s), 7.87–8.00 (3H, m), 7.68 (2H, br d), 7.52 (2H, d), 7.45 (1H, d), 7.00 (1H, s), 4.06 (2H, br t), 3.80 (3H, s), 3.10–3.35 (8H, br s), 3.05 (2H, t), 2.69 (3H, s), 2.37 (3H, s).

We claim:

1. A compound of formula (I) or a salt thereof:

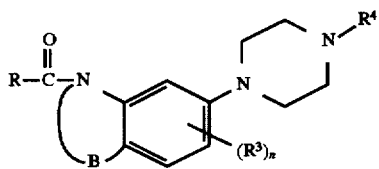

in which

R is a group of formula (i):

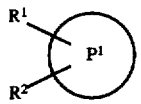

in which P$^1$ is a phenyl or a 5 to 7-membered heterocyclic ring containing 1 to 3 heteroatoms selected from oxygen, nitrogen or sulphur; and R$^1$ and R$^2$ are independently hydrogen, halogen, C$_{1-6}$alkyl, C$_{1-6}$alkoxy, hydroxyC$_{1-6}$alkyl, acyl, nitro, trifluoromethyl, cyano, SR$^5$, SOR$^5$, SO$_2$R$^5$, SO$_2$NR$^5$R$^6$, CO$_2$R$^5$, CONR$^5$R$^6$, CONR$^5$(CH$_2$)$_x$CO$_2$R$^6$, NR$^5$R$^6$, NR$^5$CO$_2$R$^6$, CR$^5$=NOR$^6$, where R$^5$ and R$^6$ are independently hydrogen or C$_{1-6}$alkyl and x is 1 to 3;

or R is a group of formula (ii):

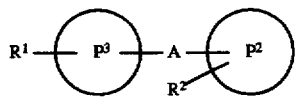

in which P$^2$ is phenyl or biphenyl;

P$^3$ is phenyl or a 5 to 7-membered heterocyclic ring containing 1 to 3 heteroatoms selected from oxygen, nitrogen or sulphur, A is a bond or a group (CH$_2$)$_p$—R$^8$—(CH$_2$)$_q$ where R$^8$ is oxygen, S(O)$_m$ where m is 0 to 2, carbonyl, CO$_2$ or CH and p and q are independently 0 to 3; and R$^1$ and R$^2$ are as defined above in formula (i);

R$^3$ is hydrogen, halogen, hydroxy, C$_{1-6}$alkyl or C$_{1-6}$alkoxy;

n is 1 or 2;

R$^4$ is hydrogen or C$_{1-6}$alkyl; and

B is —CHR$^9$CHR$^{10}$— or —CR$^9$=CR$^{10}$— where R$^9$ and R$^{10}$ are independently hydrogen or C$_{1-6}$alkyl.

2. A compound according to claim 1 in which R is a group of formula (ii).

3. A compound according to claim 2 in which P$^2$ is biphenyl and P$^3$ is an oxadiazolyl group.

4. A compound according to claim 2 in which R$^1$ and R$^2$ are C$_{1-6}$alkyl.

5. A compound according to claim 1 in which R$^3$ is C$_{1-6}$alkoxy.

6. A compound according to claim 1 in which R$^4$ is hydrogen or C$_{1-4}$alkyl.

7. A compound according to claim 1 which is:

1-[3-methyl-4-(4-pyridyl)benzoyl]-2,3-dihydro-5-methoxy-6-(4-methyl-1-piperazinyl)]-1H-indole, 1-(4-bromo-3-methylbenzoyl)-2,3-dihydro-5-methoxy-6-(4-methyl-1-piperazinyl)-1H-indole, 1-(4-bromo-3-methylbenzoyl)-5-methoxy-6-(4-methyl-1-piperazinyl)-1H-indole, 2,3-dihydro-5-methoxy-6-(4-methyl-1-piperazinyl)-1-[2'-bromo-3'-methoxythiophene-4'-ylcarbonyl]indole, 2,3-dihydro-5-methoxy-6-(4-methyl-1-piperazinyl)-1-[4'-phenoxybenzoyl]indole, 2,3-dihydro-5-methoxy-1-[4-(2-methyl-4-(5-methyl-1,2,4-oxadiazol-3-yl)phenyl) benzoyl]-6-(4-methyl-1-piperazinyl)-1H-indole, 5-methoxy-1-[4-(2-methyl-4-(5-methyl-1,2,4-oxadiazol-3-yl)phenyl)benzoyl]-6-(4-methyl-1-piperazinyl)-1H-indole, or 2,3-dihydro-5-methoxy-1-[4-(2-methyl-4-(5-methyl-1,2,4-oxadiazol-3-yl)phenyl) benzoyl]-6-(1-piperazinyl)-1H-indole, or pharmaceutically acceptable salts thereof.

8. A process for the preparation of a compound of claim 1 which comprises:

(a) coupling a compound of formula (II):

R—COL     (II)

in which R is as defined in formula (I) and L is a leaving group with a compound of formula (III):

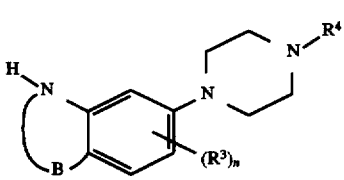

in which R$^3$, R$^4$, B and n are as defined in formula (I);

(b) for compounds where R is a group of formula (ii), A is a bond and P$^2$ is a phenyl group, reaction of a compound of formula (IV):

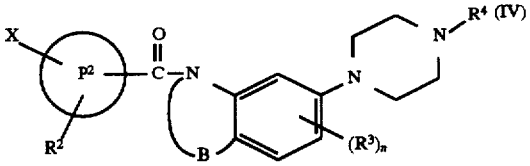

in which R$^2$, R$^3$, R$^4$ and n are as defined in formula (I), P$^2$ is phenyl and X is a leaving group with a nucleophile R$^1$—P$^3$ where R$^1$ and P$^3$ are as defined in formula (1);

(c) reaction of a compound of formula (V):

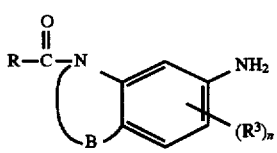

in which R, R$^3$, B and n are as defined in formula (I) with a compound of formula (VI):

 (VI)

in which $R^4$ is as defined in formula (I) and Hal is halogen, or (d) for compounds where R is a group of formula (ii) and A is a bond, reaction of a compound of formula (VII):

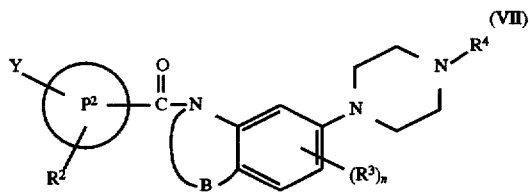 (VII)

in which $P^2$, $R^2$, $R^3$, $R^4$, B and n are as defined in formula (I) and Y is halogen or a group —$OSO_2CF_3$ with a compound of formula (VIII):

 (VIII)

in which $R^1$ and $P^3$ are as defined in formula (I), or (e) for compounds where R is a group of formula (ii) and A is a bond, reaction of a compound of formula (IX):

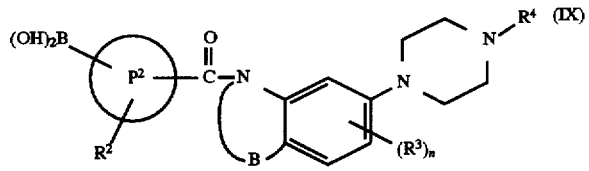 (IX)

in which $P^2$, $R^2$, $R^3$, $R^4$, B and n are as defined in formula (I) with a compound of formula (X):

 (X)

in which $R^1$ and $P^3$ are as defined in formula (I) and Y is as defined in formula (VII), and optionally after any of the above processes:

converting a compound of formula (I) into another compound of formula (I)

forming a pharmaceutically acceptable salt.

9. A pharmaceutical composition which comprises a compound according to claim 1 in association with a pharmaceutically acceptable carrier or excipient.

* * * * *